United States Patent
Hamamah et al.

(10) Patent No.: US 10,628,944 B2
(45) Date of Patent: Apr. 21, 2020

(54) METHODS FOR THREE DIMENSIONAL RECONSTRUCTION AND DETERMINING THE QUALITY OF AN EMBRYO

(71) Applicants: INSTITUT NATIONAL DE LA SANTÉ ET DE LA RECHERCHE MÉDICALE (INSERM), Paris (FR); UNIVERSITE DE MONTPELLIER, Montpellier (FR); CENTRE HOSPITALIER UNIVERSITAIRE DE MONTPELLIER, Montpellier (FR)

(72) Inventors: Samir Hamamah, Montpellier (FR); Elodie Scalici, Montpellier (FR)

(73) Assignees: INSERM (INSTITUT NATIONAL DE LA SANTÉ ET DE LA RECHERCHE MÉDICALE), Paris (FR); UNIVERSITE DE MONTPELLIER, Montpellier (FR); CENTRE HOSPITALIER UNIVERSITAIRE DE MONPELLIER, Montepllier (FR)

( * ) Notice: Subject to any disclaimer, the term of this patent is extended or adjusted under 35 U.S.C. 154(b) by 47 days.

(21) Appl. No.: 15/322,353

(22) PCT Filed: Jul. 1, 2015

(86) PCT No.: PCT/IB2015/001346
§ 371 (c)(1),
(2) Date: Dec. 27, 2016

(87) PCT Pub. No.: WO2016/001754
PCT Pub. Date: Jan. 7, 2016

(65) Prior Publication Data
US 2017/0140535 A1 May 18, 2017

Related U.S. Application Data

(60) Provisional application No. 62/019,574, filed on Jul. 1, 2014.

(51) Int. Cl.
| | |
|---|---|
| *A61B 17/435* | (2006.01) |
| *G06T 19/00* | (2011.01) |
| *G06T 7/00* | (2017.01) |
| *C12N 5/073* | (2010.01) |
| *G06T 11/00* | (2006.01) |

(52) U.S. Cl.
CPC .......... *G06T 7/0014* (2013.01); *A61B 17/435* (2013.01); *C12N 5/0604* (2013.01);
(Continued)

(58) Field of Classification Search
CPC ... A61B 17/425; A61B 17/435; G06T 7/0012; G06T 7/0014; G06T 7/0016; G06T 2207/30044
See application file for complete search history.

(56) References Cited

U.S. PATENT DOCUMENTS

2013/0337487 A1* 12/2013 Loewke ............ G01N 33/4833
435/29

FOREIGN PATENT DOCUMENTS

| WO | 2010/151221 A1 | 12/2012 |
| WO | 2012/163363 A1 | 12/2012 |

OTHER PUBLICATIONS

M. Meseguer et al: "The use of morphokinetics as a predictor of embryo implantation", Human Reproduction, vol. 26, No. 10, Aug. 9, 2011, pp. 2658-2671.
(Continued)

*Primary Examiner* — Carrie R Dorna
(74) *Attorney, Agent, or Firm* — W&C IP

(57) ABSTRACT

The present invention relates generally to the fields of reproductive medicine. More specifically, the present invention relates to methods and devices for determining the
(Continued)

Figure 1:
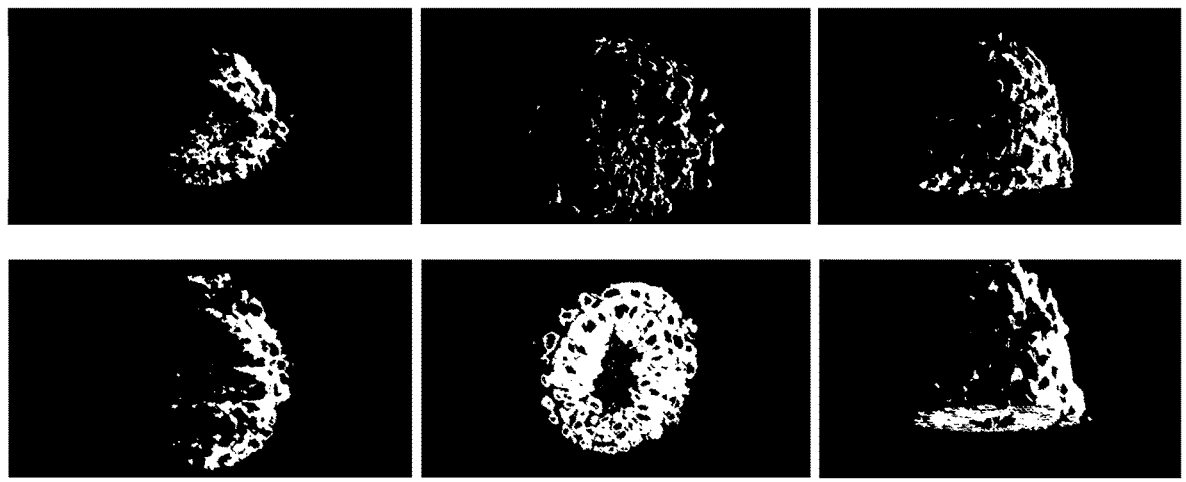

quality of an embryo. More specifically, the present invention relates to the use of three dimensional reconstructions for determining the quality of an embryo.

8 Claims, 8 Drawing Sheets

(52) U.S. Cl.
CPC .......... *G06T 7/0012* (2013.01); *G06T 11/003* (2013.01); *G06T 19/00* (2013.01); *G06T 2207/10056* (2013.01); *G06T 2207/10088* (2013.01); *G06T 2207/10101* (2013.01); *G06T 2207/30044* (2013.01); *G06T 2210/41* (2013.01)

(56) References Cited

OTHER PUBLICATIONS

Michael Weber et al: "Light sheet microscopy for real-time developmental biology", Current Opinion in Genetics & Development, vol. 21, No. 5, Sep. 30, 2011, pp. 566-572.

Keller P J et al: "Reconstruction of zebrafish early embryonic development by scanned light sheet microscopy", Science, vol. 322, No. 5904, Nov. 14, 2008, pp. 1065-1069.

K. Kirkegaard et al: "Time-lapse monitoring as a tool for clinical embryo assessment", Human Reproduction, vol. 27, No. 5, Mar. 14, 2012, pp. 1277-1285.

Sharpe J et al: "Optical Projection Tomography as a Tool for 3D Microscopy and Gene Expression Studies", Science, vol. 296, Apr. 19, 2003, pp. 541-545.

Tomer Raju et al: Quantitative high-speed imaging of entire developing embryos with simultaneous multiview light-sheet microscopy, Nature Methods, vol. 9, No. 7, Jul. 2012, pp. 755-763.

Patazis Periklis et al: "Advances in whole-embryo imaging: a quantitative transition in underway", Nature Reviews Molecular Cell Biology, vol. 15, No. 5, May 2014, pp. 327-339.

Connie C Wong et al: "Non-invasive imaging of human embryos before embryonic genome activation predicts development to the blastocyst stage", Nature Biotechnology, vol. 28, No. 10, Oct. 1, 2010, pp. 1115-1121.

Lhuaire Martin et al: "Human developmental anatomy; Microscopic magnetic resonance imaging ([mu]MRI) of four human embryos (from Carnegie Stage 10 to", Annals of Anatomy, Jena, DE, vol. 196, No. 6, Jul. 29, 2014, pp. 402-409.

* cited by examiner

1. Microscopic 2D-visualization: image sections of optical microscopy
2. 3D reconstruction Software to perform Multi Planar Reconstructions and 3D Volume Rendering
3. 3D Printing First human embryo « ex vitro »

- To improve embryo observation and selection for transfer
- Fragmentation (%, topography, volumetric measure...)
- Cleavage axis
- 3D cell repartition...

The best optical approach

Microscopy using like sheet based on SPIM

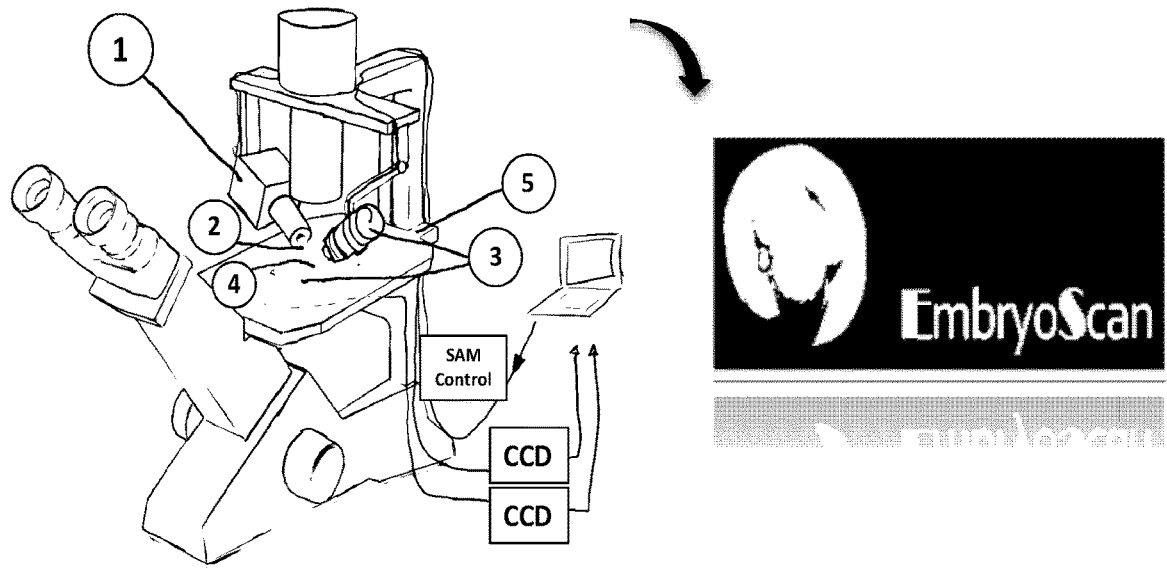

Adapted optical system on conventionnal IVF microscopy

Figure 6D

Biological interests

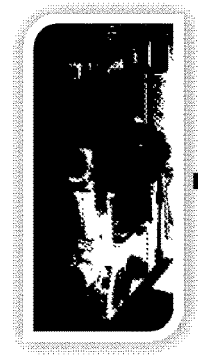

➤ Currently:

- Embryo observation in a single plane
- 3D mental reconstruction operator-dependant

➤ By using EmbryoScan:

- 3D global observation of human embryo
- Conservation of images
- Possibility to increase delay of reflection
- Collegial decision (staff)
- Telemedicine

Figure 6E

METHODS FOR THREE DIMENSIONAL RECONSTRUCTION AND DETERMINING THE QUALITY OF AN EMBRYO

FIELD OF THE INVENTION

The present invention relates generally to the field of reproductive medicine. More specifically, the present invention relates to methods and devices for determining the quality of an embryo.

BACKGROUND OF THE INVENTION

Currently, embryo selection for transfer relies on morphological criteria evaluation with optical microscopy in Assisted Reproductive Technology (ART). The parameters classically involved in embryo selection are: i) morphology and fertilization of oocyte having generated embryo, ii) number and size of blastomeres, iii) cytoplasmic appearance of blastomeres, iv) fragmentation rate and v) multinucleation presence. This morphological approach is based exclusively on subjective observations of embryo morphology, dependent operator and shows limitations to predict successful pregnancy in ART (Guerif et al., 2007). Indeed, currently, 85% of embryos obtained in vitro and selected for replacement on morphological criteria lead to implantation failures. This result is completely disappointing and suggests that the limited 2D-visualization of human oocyte and embryo with optical microscopy lacks accuracy. Therefore, there is a reliable need in ART to improve human oocyte and embryo observation during their early preimplantation development and subsequently increase ART success.

Recently, a new method based on time-lapse imaging has been developed for the acquisition of embryo morphokinetic data to help such selection (Meseguer et al., 2011; Herrero and Meseguer, 2013). Nevertheless, time-lapse systems do not improve embryo morphology evaluation compared to optical microcopy since embryos contained in individual wells are observed only in 7 focal planes. Indeed, a major limitation of these systems is the inability to rotate or roll spherical oocyte and embryos making it difficult to assess morphology especially in the case of a high fragmentation rate or blastocyst stage. Moreover, regular purchase images requires light embryo. Even if the light is relatively short in these systems, an exposure time as short as possible associated with a wavelength longer closely as possible should be preferred.

The use of 3D technologies represents an innovative and attractive way in ART to develop new precious tools for studying human oocyte and early embryo and subsequently for better understanding the ART failures in the daily practice. Indeed, it seems very difficult to analyze in detail a spherical biological structure, such as human oocyte and embryo, only in 2D-planes. The constraints of the optical microscopy force us limit ourselves in human oocyte and embryo observation and 3D imaging methods could allow a sophisticated morphological assessment like in mouse model (Nieman et al., 2011). Other numerous morphological parameters could be studied with 3D technologies such as 3D pronuclei position in oocyte, 3D fragmentation repartition, 3D blastomeres cleavage axis or 3D cells repartition in the embryo. The main aim of the improvement of human oocyte and embryo observation by 3D technologies is improving ART success.

In the past years, 3D reconstructions of mouse embryos required dissections to obtain a series of histological and fixed sections in order to study embryo anatomical organization and characterize mouse morphological phenotypes (Kaufman et al., 1997; Wong et al., 2012; Wong et al., 2014). Nowadays, one of the challenges of the optical imaging is to observe in 3D the biological structures and organisms in compatible conditions for the pursuit of their development. Therefore, recently, new technologies in optical imaging field, have been developed to perform sections of viable embryos in some species and to allow a non-invasive 3D reconstruction of these embryos.

Among these new optical imaging systems, the optical coherence tomography (OCT) is a non-invasive emerging technique for biological media with micrometer-scale resolution used principally in ophthalmology. A new and original approach of OCT called full-field OCT has been proposed recently by a research team and is based on white-light interference microscopy. Full-field OCT allows to obtain tomographic pictures by combination of interferometric images recorded by a detector array such as CCD camera. Compared to conventional OCT, full-field OCT acquires tomographic images in transverse orientation with ultrahigh resolution (~1 µm) using a simple halogen lamp. Interestingly, the performance of this technology has been used in embryology and developmental biology for 3D imaging of ex-vivo specimens. Indeed, 3D reconstructions of mouse embryo are easy performed with the same resolution than in standard histological method. Moreover, image acquisitions are fast and do not require sample preparation and dissection in thin sections after fixation compared to histological sections.

Light sheet microscopy including Selective Plane Illumination Microscopy (SPIM) is also a new technique in which the illuminated plane in a sample is the only being imaged, associated with a virtual elimination of background signal and a drastic reduction of the amount of light required to explore the sample. Indeed, this technique reduces phototoxic effects in live samples and allows to see biological structures in 3D, in live and in real time without harmful effects and damaging on them (Huisken et al., 2004, Huisken, 2012). This concept is based on illuminating the sample only with thin slices of light in a focal plane, and photo bleaching is decreased to a minimum. Therefore, light sheet microscopy constitutes an ideal tool for non-destructive imaging of fragile or viable samples. Regarding to embryology and development biology applications, light sheet microscopy (including SPIM) appears to be an attractive tool to image 3D embryos at high resolution with high acquisition speed while being minimally invasive. 3D early zebrafish embryo and 3D embryonic development of *Drosophila melanogaster* reconstructions illustrate the potential of SPIM technique in developmental biology (Huisken et al., 2004; Keller et al., 2008; Huisken and Stainier, 2009; Weber and Huisken, 2011; Kaufmann et al., 2012; Krzic et al., 2012, Huisken, 2012).

Therefore, optical microscopy allows performing 3D reconstructions and printing of mouse or human embryos from several focal planes. Moreover, OCT and light sheet microscopy (including SPIM) represent the best attractive innovations to develop non-invasive image acquisitions of human oocyte and embryo for 3D reconstructions and printing. The applications of these new optical imaging methods remains to be tested in human embryology for a sophisticated observation of spherical oocyte and embryo obtained in vitro.

Furthermore, several research teams have proposed an atlas book containing 3D mouse embryo reconstructions using magnetic resonance imaging but most of the time, they did not studied embryos at the early stages. The use of micro magnetic resonance imaging (µMRI) for 3D human oocyte and embryo reconstruction could be also an attractive way for oocyte and embryo morphology assessment, but nowadays, the image spatial resolution is not sufficient even at high field (even at 9.4 T).

Recently, the emergence of 3D printing and its application have expanded in human medicine (Rengier et al., 2010; Hespel et al., 2014). Indeed, these recent technological advances allow to create complex structures such as human cartilage tissue, heart valves, bone models or cranioplasty implant using 3D printer (Kim et al., 2012; Visser et al., 2013; Cui et al., 2014; Nakayama et al., 2014; Unger et al., 2014. Hochman et al., 2014; Tan et al., 2014). Like in surgery, one recent study reported the reproduction of zebrafish embryos and larvae models using a 3D printer (Masselink et al., 2014). Therefore, the 3D printing of human oocyte and embryo could allow the creation of several models of a more realistic nature, representing real oocyte and embryo development. Moreover, these human oocyte and embryo models may represent informative, pedagogic training and updating tools for embryologist staff, patients and students.

SUMMARY OF THE INVENTION

The present invention relates generally to the fields of reproductive medicine. More specifically, the present invention relates to methods and devices for determining the quality of an embryo. More specifically, the present invention relates to the use of three dimensional reconstructions for determining the quality of an embryo.

DETAILED DESCRIPTION OF THE INVENTION

The present invention relates to the methods allowing 3D reconstruction and 3D printing of human oocytes and embryos from serially image sections in order to improve morphology evaluation at different stages of their in vitro development. The inventors demonstrate that 3D reconstruction and 3D printing represent non-invasive innovations in ART in order to help the best embryo selection. Moreover, the inventors demonstrate that 3D human or mouse embryos reconstructions and printings can be performed from standard optical microscopic sections. New 3D technologies as OCT or light sheet microscopy (SPIM for example) could allow non-invasive image acquisitions with better quality for 3D reconstructions of viable human oocyte and embryo. High spatial resolution Micro Magnetic Resonance Imaging also represents an attractive way to examine human oocyte and embryo morphology. The use of 3D technologies for embryo selection lead to an increase of ART success and represent at the same time a pedagogic approach for technical and medicine formation and an informative tool for patients undergoing ART procedure.

Accordingly, the present invention relates to an in vitro non invasive method for determining the quality of an embryo comprising the steps of:

i) providing serially image sections of said embryo, ii) performing three dimensional reconstruction of said embryo, and iii) determining embryo morphology, fragmentation repartition, blastomeres cleavage axis and/or cells repartition on said three dimensional reconstruction.

In some embodiments, the present invention relates to an in vitro non invasive method for determining the quality of an oocyte comprising the steps of:

i) providing serially image sections of said oocyte, ii) performing three dimensional reconstruction of said oocyte, and iii) determining pronuclei position in oocyte on said three dimensional reconstruction.

In one embodiment, the present invention relates to the in vitro non invasive method for determining the quality of an embryo or an oocyte of the invention wherein the step iii) is performed using informatics automatic segmentation tools.

As used herein the term "embryo" has its general meaning in the art and refers to a fertilized oocyte or zygote. The term "embryo" also refers to cells in all stages of development from a fertilized oocyte or zygote up to the 5 or 6 days (blastocyst stage). Said fertilization may intervene under a classical in vitro fertilization (cIVF) conditions or under an intracytoplasmic sperm injection (ICSI) procedure. Examples of embryos that may be assessed by the methods of the invention include 1-cell embryos (also referred to as zygotes), 2-cells embryo, 3-cells embryo, 4-cells embryo, 5-cells embryo, 6-cells embryo, 8-cells embryo, etc. typically up to and including 16-cells embryo, any of which may be derived by any convenient manner, e.g. from an oocyte that has matured in vivo or from an oocyte that has matured in vitro. As used herein, the term "blastocyst" refers to the structure formed in the early embryogenesis of mammals, after the formation of the morula. It possesses an inner cell mass (ICM), or embryoblast, which subsequently forms the embryo, and an outer layer of cells, or trophoblast, which later forms the placenta. The trophoblast surrounds the inner cell mass and a fluid-filled blastocyst cavity known as the blastocoele. The human blastocyst comprises 70-100 cells. Blastocyst formation begins at day 5/6 after fertilization in humans.

According to the invention, the oocyte may result from a natural cycle, a modified natural cycle or a stimulated cycle for cIVF or ICSI. The term "natural cycle" refers to the natural cycle by which the female or woman produces an oocyte. The term "modified natural cycle" refers to the process by which, the female or woman produces an oocyte or two under a mild ovarian stimulation with GnRH antagonists associated with recombinant FSH or hMG. The term "stimulated cycle" refers to the process by which a female or a woman produces one or more oocytes under stimulation with GnRH agonists or antagonists associated with recombinant FSH or hMG.

The term "classical in vitro fertilization" or "cIVF" refers to a process by which oocytes are fertilised by sperm outside of the body, in vitro. IVF is a major treatment in infertility when in vivo conception has failed. The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm, and occasionally as a method of in vitro fertilization, especially that associated with sperm donation.

By "determining the quality of an oocyte or an embryo" it is meant that the method of the invention aims at determining whether an oocyte or an embryo is competent in the context of in vitro fertilization. The method of the invention allows the assessment of the ability of an oocyte or an embryo to perform successfully either or both in terms of conferring a high pregnancy rate and/or resulting in a healthy person. Accordingly the method of the invention allows selection of the embryo with low fragmentation rate that is able to give rise to pregnancy.

The term "competent oocyte" refers to a female gamete or egg that when fertilized produces a viable embryo with a high implantation rate leading to pregnancy.

The term "competent embryo" refers to an embryo with a high implantation rate leading to pregnancy. The term "high implantation rate" means the potential of the embryo when transferred in uterus, to be implanted in the uterine environment and to give rise to a viable fetus, which in turn develops into a viable offspring absent of a procedure or event that terminates said pregnancy.

The method of the invention is applicable preferably to women but may be applicable to other mammals (e.g., primates, dogs, cats, pigs, cows, mouse . . . ).

The term "three dimensional recontruction" has its general meaning in the art and relates to the reconstitution of the oocyte or the embryo in three dimensions.

Any methods well known in the art may be used by the skilled artisan in the art for providing serial image sections. For example, the method described in the example may be used. Providing serially image sections may be performed from standard optical microscopy or light sheet microscopy (for example Selective Plane Illumination Microscopy (SPIM)) or Optical Coherence Tomography (OCT) or Magnetic Resonance Micro Imaging (µMRI).

Any methods well known in the art may be used by the skilled artisan in the art for performing 3D reconstruction. For example, the method described in the example may be used. Performing 3D reconstruction from image sections may be performed using a software able to import stacks of images coming from the different modalities of imaging (classical microscopy, light sheet microscopy (for example SPIM), OCT, micro-MRI). This software can perform Multiplanar Reconstructions (MPR), Volume Rendering (VR), segmentation of the objects of interest (manual segmentation or semi-automatic or automatic informatics segmentation), automatic identification of blastomeres and fragments with volumetric measures, extraction of 3D surfaces and export for 3D printing.

In a particular embodiment the method of the invention comprises the steps of:

i) determining pronuclei position in oocyte, determining embryo morphology, fragmentation repartition, blastomeres cleavage axis and/or cells repartition on said 3D reconstruction, ii) comparing the pronuclei position in oocyte, embryo morphology, fragmentation repartition, blastomeres cleavage axis and/or cells repartition on said 3D reconstruction determined at step i) with a control, and iii) concluding that the oocyte or the embryo is competent when the pronuclei position in oocyte, embryo morphology, fragmentation repartition, blastomeres cleavage axis and/or cells repartition on said 3D reconstruction determined at step i) are identical to the same criteria in competent oocyte or competent embryo, and concluding that the oocyte or the embryo is non competent when the pronuclei position in oocyte, embryo morphology, fragmentation repartition, blastomeres cleavage axis and/or cells repartition on said 3D reconstruction determined at step i) are identical to the same criteria in non competent oocyte or non competent embryo.

In one embodiment the control is a competent oocyte or a competent embryo. In another embodiment the control is a non competent oocyte or a non competent embryo.

In a further aspect, the present invention relates to an in vitro non: invasive method for determining the quality of an embryo comprising the steps of:

i) providing serially image sections of said embryo, ii) performing three dimensional reconstruction of said embryo, and iii) determining embryo morphology by determining the number of blastomeres, blastomere regularity and fragmentation rate, iv) and concluding that the embryo is competent if having 6 to 8 blastomeres, blastomeres of regular size and low fragmentation rate (equal or less than 25%), and concluding that the embryo is non-competent if having fewer blastomeres (<6 cells at day 3), blastomeres of irregular size and high fragmentation rate (more than 25%).

The method of the invention is particularly suitable for reaching a clinical decision. As used herein the term "clinical decision" refers to any decision to take or not take an action that has an outcome that affects the health or survival of the embryo. In particular, in the context of the invention, a clinical decision refers to a decision to implant or not the embryo of in the uterus of the patient. In particular the method as above described will thus help embryologist to avoid the transfer in uterus of embryos with a poor potential for pregnancy outcome. The method as above described is also particularly suitable for avoiding multiple pregnancies by selecting the competent oocyte and the competent embryo able to lead to an implantation and a pregnancy and therefore fewer embryos could be transferred at each cycle, resulting in a decreased incidence of multiple pregnancies.

In a further aspect, the invention relates to a method for enhancing the pregnancy outcome of a patient comprising the steps consisting of i) providing a plurality of embryos, ii) determining the quality of the embryo by performing the method according to the invention, iii) selecting the most competent embryo, and iv) implanting the embryo selected at step iii) in the uterus of said patient.

In a further aspect, the invention relates to a method of implanting a competent embryo in a patient undergoing in vitro fertilization, comprising the steps of:

a) collecting oocytes from said patient;

b) generating embryos from said oocytes by fertilizing said oocytes in vitro;

c) determining the quality of the embryo by performing the method according to the invention; and d) implanting said embryo having a higher probability of being competent in said patient.

The present invention also relates to a device for implementing the method of the invention comprising means for providing serially image sections of step i), means for performing three dimensional construction of step ii), and means for determining pronuclei position in oocyte, embryo morphology, fragmentation repartition, blastomeres cleavage axis and/or cells repartition on said three dimensional reconstruction determined at step i).

The present invention also relates to a method of producing or printing an oocyte or an embryo comprising the steps of:

i) providing serially image sections of said oocyte or embryo, ii) performing three dimensional reconstruction of said oocyte or embryo, iii) determining pronuclei position in oocyte, determining embryo morphology, fragmentation repartition, blastomeres cleavage axis and/or cells repartition on said three dimensional reconstruction, and iv) three dimensional printing of said oocyte or said embryo.

The present invention also relates to an artificially produced or three-dimensional printed oocyte or embryo performed by the method according to the invention.

Any methods well known in the art may be used by the skilled artisan in the art for three dimensional printing. For example, the method described in the example may be used.

The invention will be further illustrated by the following figures and examples. However, these examples and figures should not be interpreted in any way as limiting the scope of the present invention.

FIGURES

FIG. 1: 3D mouse embryo reconstruction and visualization from fixed histological image sections of optical microscopy.

Figure 2:
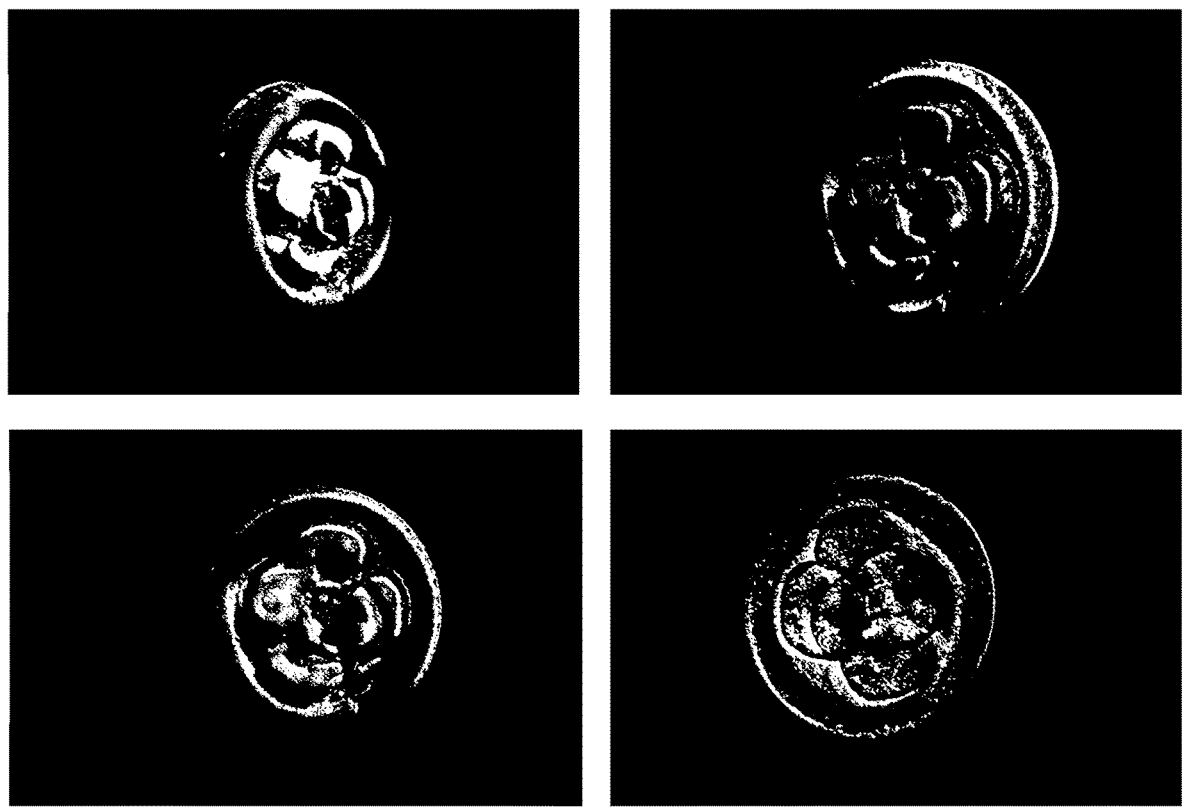

FIG. 2: Non-invasive 3D reconstruction and visualization of viable human embryo from images section of optical microscopy in IVF laboratory.

Figure 3:
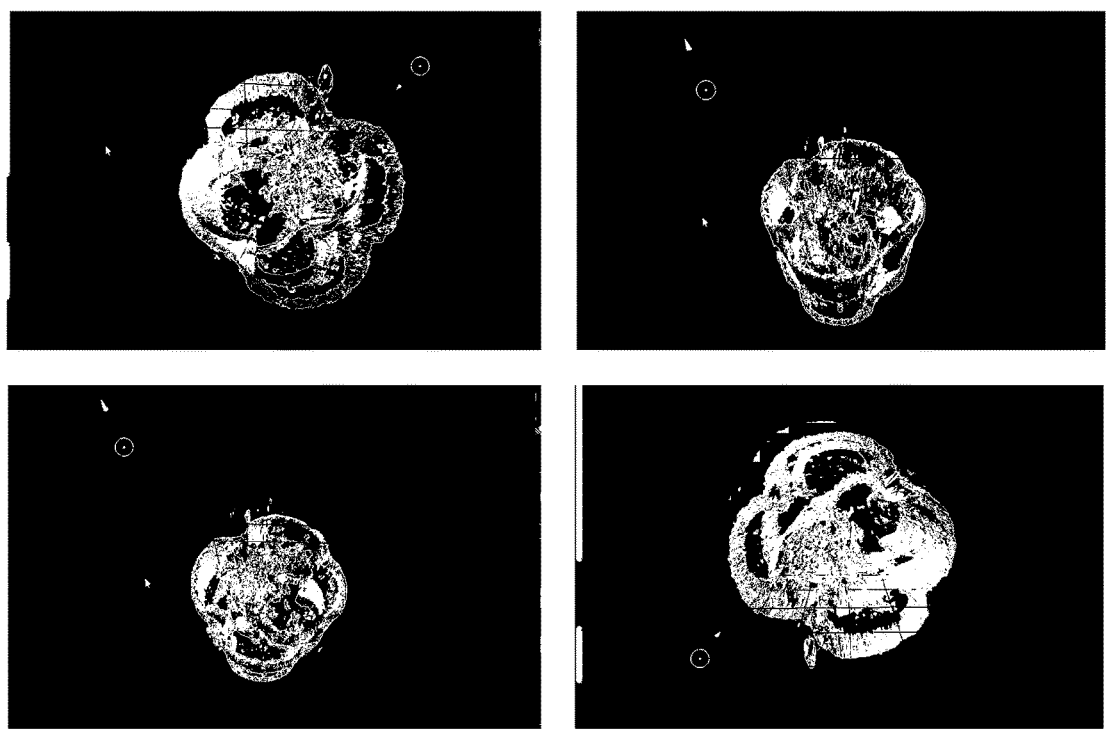

FIG. 3: A non-invasive 3D reconstruction of viable human embryo at day 3 performed from 20 section planes of standard optical microscopy in IVF laboratory.

Figure 4:
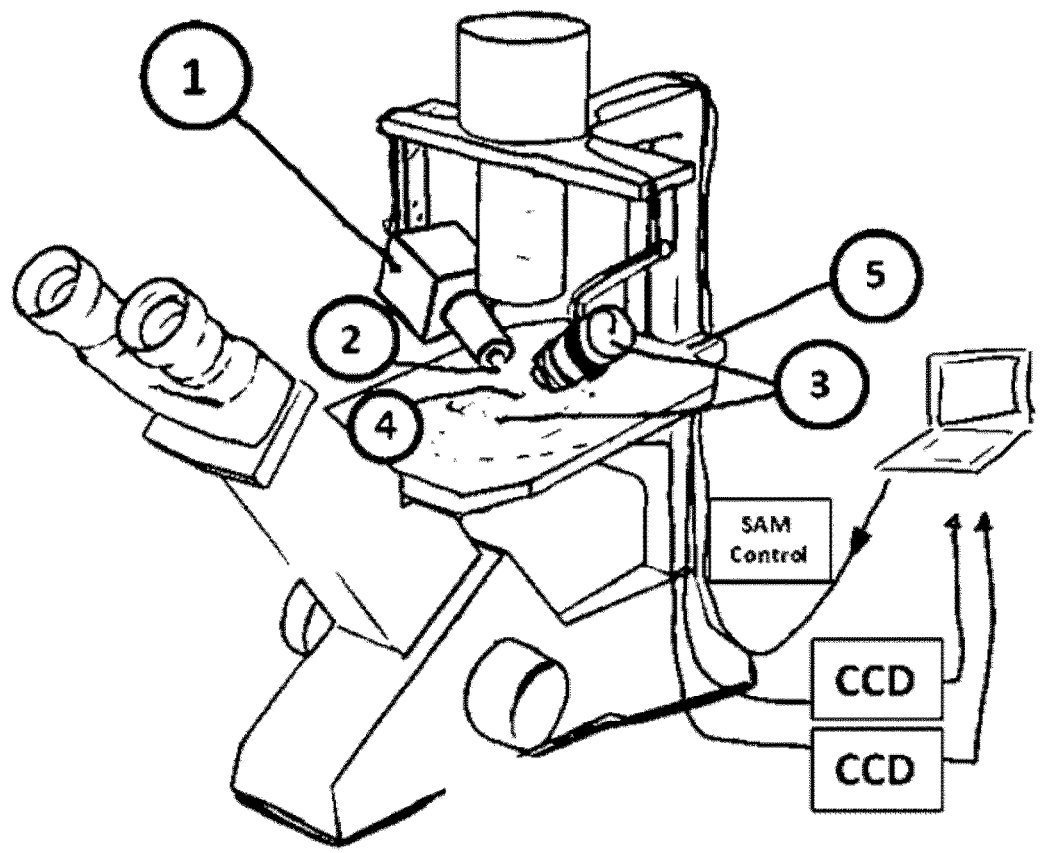
Figure 5A:
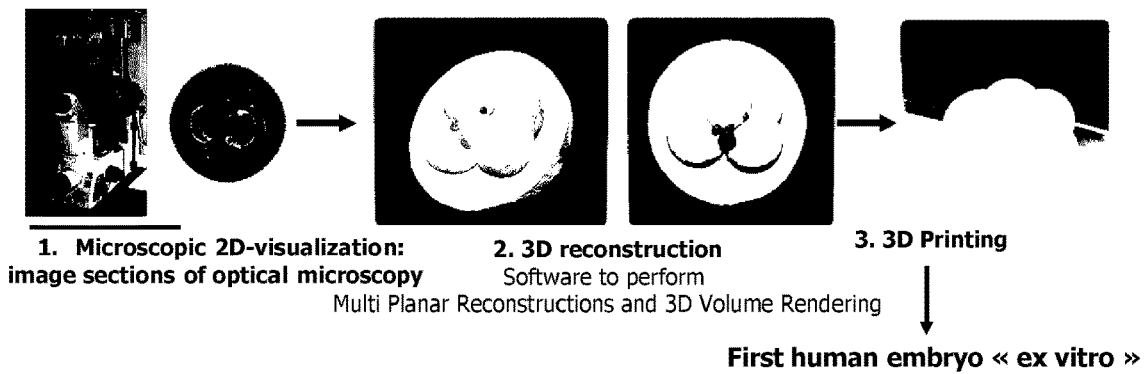
Figure 5B:
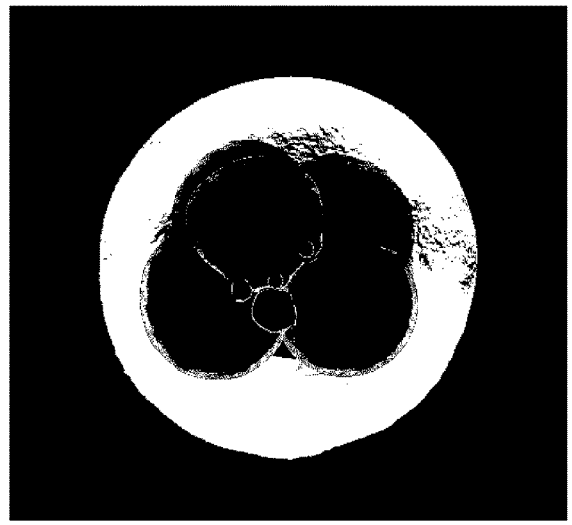
Figure 5C:
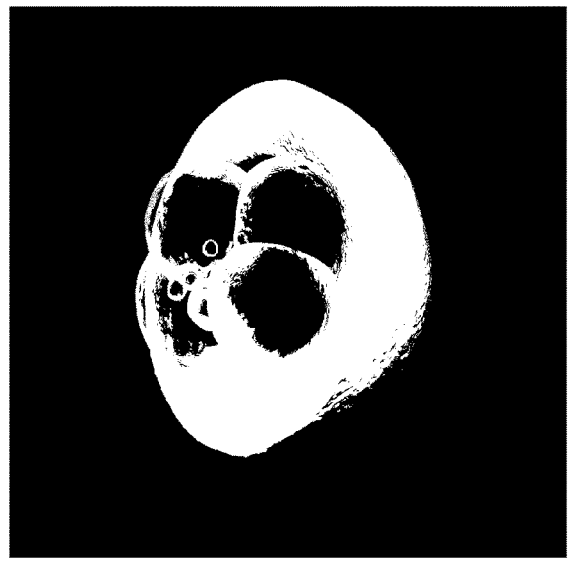
Figure 5D:
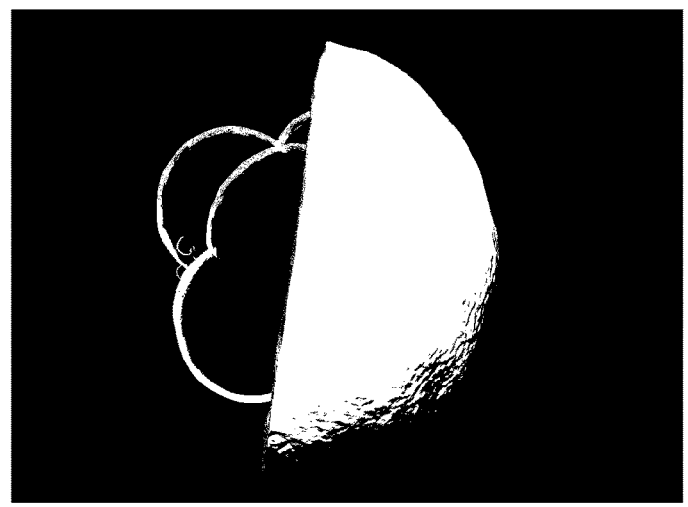
Figure 5E:
Figure 5F:
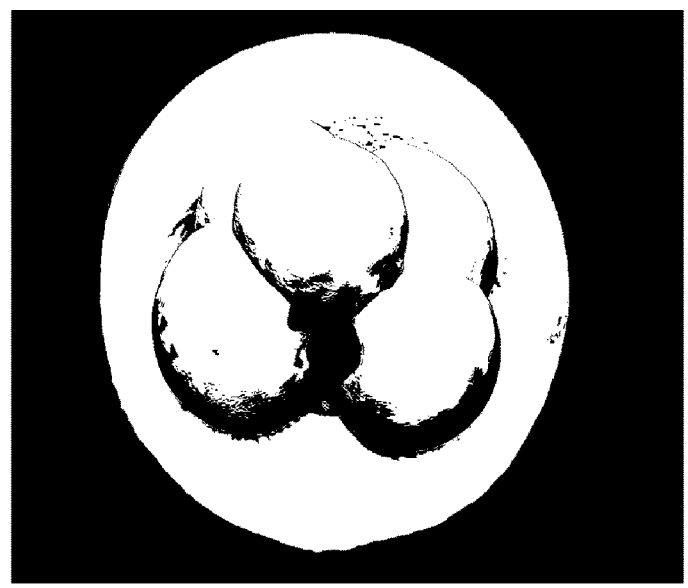
Figure 5G:
Figure 5H:
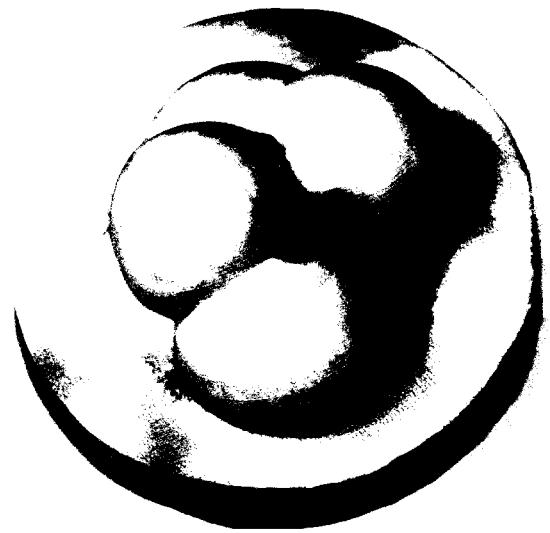
Figure 5I:
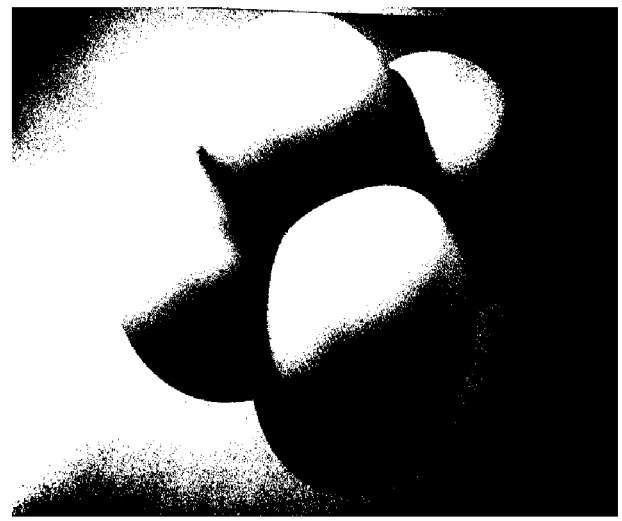

FIG. 4: Example of a microscope using like sheet based on SPIM.

FIG. 5: 3D human embryos reconstruction and printing.

FIG. 6: A. Limits of embryo conventional observation by optical microscopy and the insufficiency of morphological observation to predict implantation and pregnancy rates. B. Optical microscopy and 3D reconstruction and printing. C. Two optical microscopic methods, optical coherence tomography (OCT) and light sheet microscopy including Selective Palne illumination Microscopy (SPIM). D. An adapted optical system on conventionnal IVF microscopy. E. The biological interests of using embryoscan.

EXAMPLES

Example 1

Embryoscan.

The present invention relates to the methods for three dimensional (3D) reconstruction and 3D printing of human oocytes and embryos. More precisely, it pertains to the use of 3D technologies as new and innovative tools to improve oocyte and embryo morphology assessment during their preimplantation development in vitro.

The present invention is based on 3D reconstruction and 3D printing of human oocytes and embryos. These 3D technologies can be used for assessing embryo morphology and improving embryo selection in order to increase ART success. Moreover, 3D technologies represent an informative tool for training, updating of embryologist staff and for patients undergoing ART procedure.

This invention comprises the steps consisting of:
i) Providing serially image sections of human oocyte and embryo from standard optical microscopy or light sheet microscopy (for example SPIM) or Optical Coherence Tomography (OCT) or Magnetic Resonance Micro Imaging (µMRI).
ii) Performing 3D reconstruction of human oocyte and embryo from image sections using a software able to import stacks of images coming from the different modalities of imaging (classical microscopy, light sheet microscopy (for example SPIM), OCT, micro-MRI). This software can perform Multiplanar Reconstructions (MPR), Volume Rendering (VR), segmentation of the objects of interest, (manual segmentation or semi-automatic or automatic informatics segmentation), automatic identification of blastomeres and fragments with volumetric measures, extraction of 3D surfaces and export for 3D printing.
iii) Analyzing oocyte and embryo morphology on 3D reconstructions.
iiii) Performing 3D printing from 3D human oocyte and embryo reconstructions.
iiiii) Using 3D printed models for information, training and medicine formation.

3D mouse embryo reconstruction and visualization from fixed histological image sections of optical microscopy. Using a stack of 57 TIFF images obtained in classical optical microscopy from a mouse embryo (TS7), it is possible to make MultiPlanar Reconstructions (MPR) and 3D Volume Rendering. Volume Rendering is a 3D technique of visualization well known in radiology to emphasize CT Scan and MM results. Volume Rendering can be applied on other samples of images than DICOM (including TIFF or JPEG images) to have 3D informations of the specimen (transparency can be modified to better see the nuclei for example) (FIG. 1).

Non-invasive 3D reconstruction and visualization of viable human embryo from images section of optical microscopy in IVF laboratory (FIG. 2).

A non-invasive 3D reconstruction of viable human embryo at day 3 was performed from 20 section planes of standard optical microscopy in IVF laboratory. Modifying the focus, it is possible to obtain a stack of images that can be imported in a 3D vizualisation software to perform Multi Planar Reconstructions and Volume Rendering (FIG. 3).

The inventors also performed:

3D printed model obtained from 3D reconstruction of viable human embryo.

3D human oocyte and embryo reconstruction and printing: pedagogic and informative tools for technical training and formation in laboratory.

3D human oocyte and embryo reconstruction and printing: informative tools for patients undergoing IVF program.

3D human oocyte and embryo printing models and derivatives market.

Creation of a web database with 3D reconstructions of human embryo and oocyte.

3D human embryos reconstruction and printing are illustrated in FIG. 5A-I.

Figure 6A:
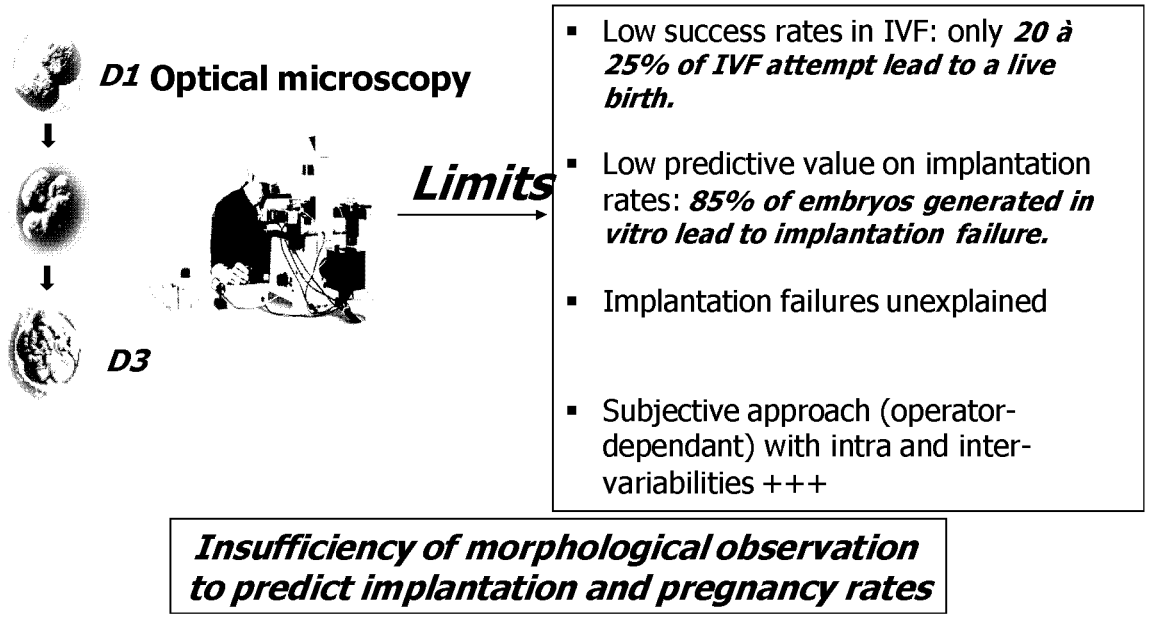
Figure 6B:
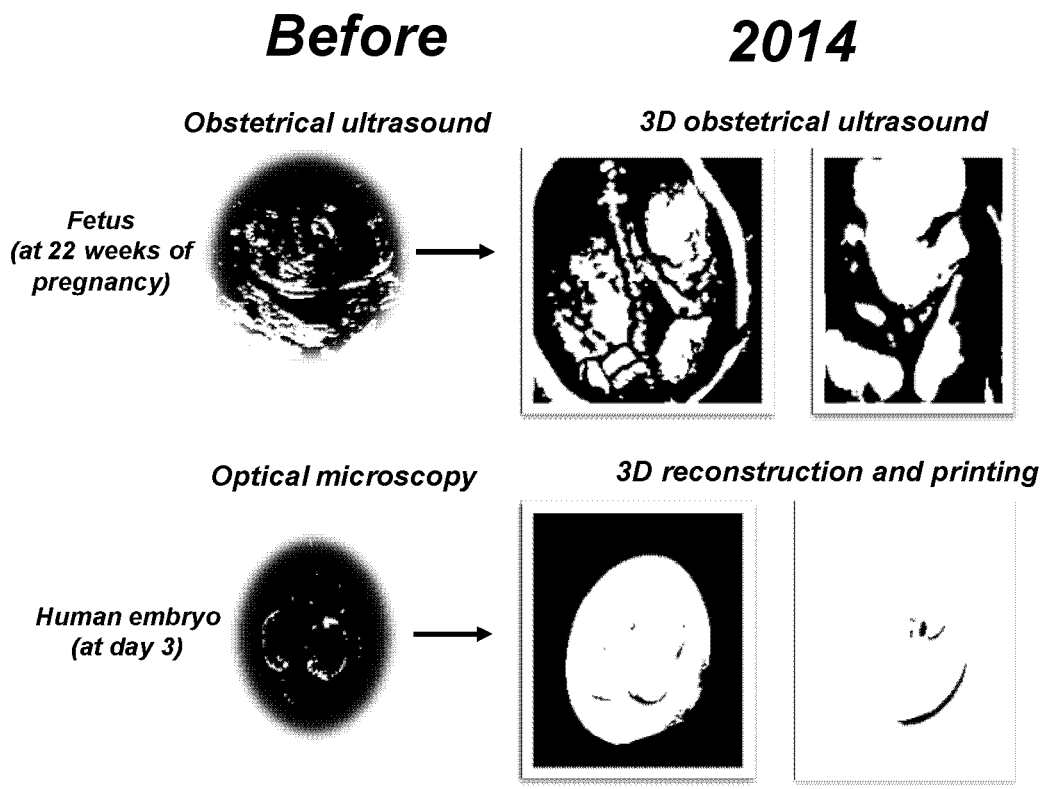
Figure 6C:
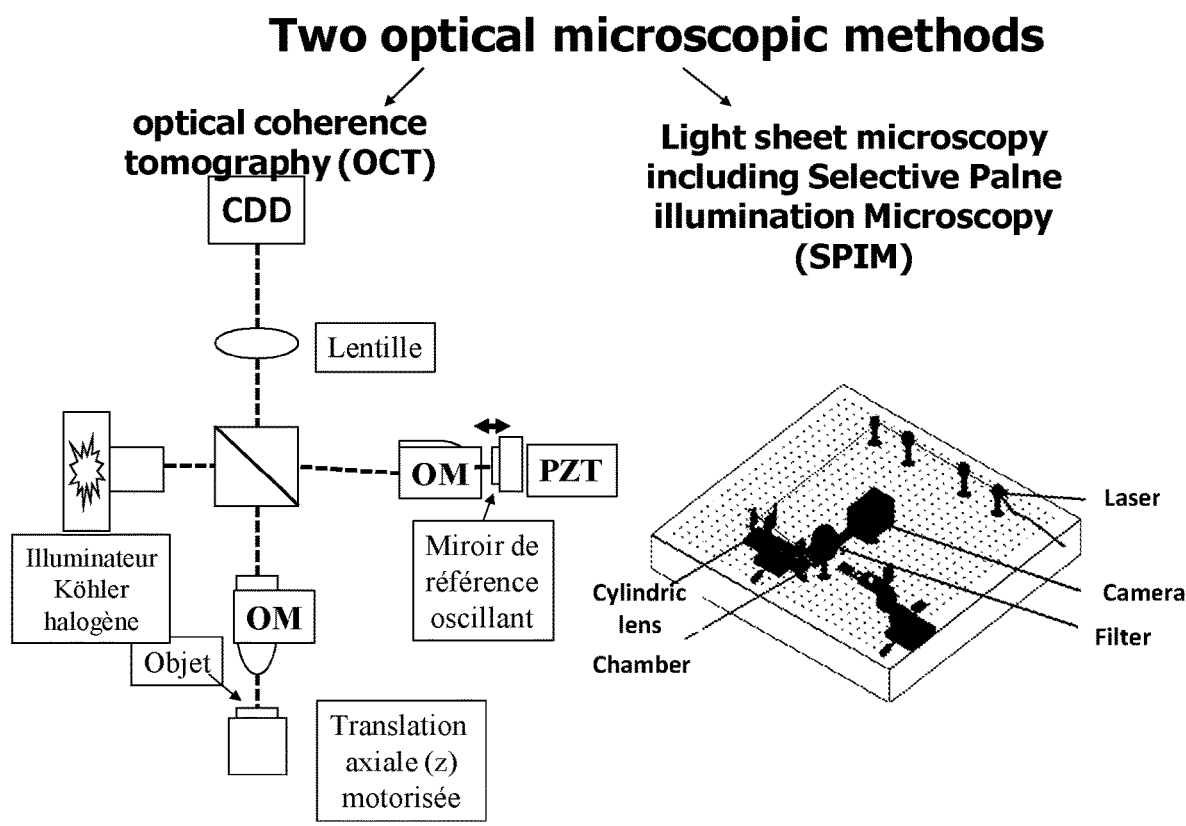

The inventors show in FIG. 6A the limits of embryo conventional observation by optical microscopy and the insufficiency of morphological observation to predict implantation and pregnancy rates. The inventors illustrate optical microscopy and 3D reconstruction and printing in FIG. 6B, two optical microscopic methods, optical coherence tomography (OCT) and light sheet microscopy including Selective Palne illumination Microscopy (SPIM) in FIG. 6C, an adapted optical system on conventional IVF microscopy FIG. 6D and the biological interests of the invention (embryoscan) in FIG. 6E.

The invention presents important clinical and economic impacts by improving:
Embryo selection with a best morphological assessment
Implantation and pregnancy rates
IVF cost-effectiveness
Conclusions:
3D reconstructions and 3D printing of human oocyte and embryo represent new technologies and innovations to improve oocyte and embryo morphology assessment in ART. These innovative 3D technologies could provide a supplemental and precious help for viable embryo selection in order to increase ART success.

Example 2

Example of a microscope using like sheet based on SPIM. An optical device (1) produces a light sheet (2), illumining a single plane of the object (4). Two objectives (3), placed at 90° relative to the light sheet beam, are each connected to CCD cameras. A computer receives the images from the two cameras and pilots automatically the displacements of the motorized xyz stage (5) to make stacks of pictures of the different planes of the embryo alternatively illuminated by the SPIM. The pictures are finally sent into a visualization software: it mixes the pictures of the two cameras and shows the result in Multiplanar Reconstruction (MPR) and 3D (VR) (FIG. 4).

Example 3

In Vitro Fertilization, Embryo Quality Classification and IVF Outcomes.

Ovulation is induced by a single injection of 250 μg of human chorionic gonadotropin (OVITRELLE®; Merck Serono). Oocyte retrieval is performed by transvaginal ultrasound-guided aspiration 36 hours after the injection and each pre-ovulatory follicle is aspirated individually without flushing.

Cumulus-oocyte complexes are isolated for conventional IVF or ICSI procedures. Before microinjection for ICSI, oocyte maturity is assessed after denudation. Oocytes are individually cultured in a 30 μl microdroplet of culture medium (VITROLIFE®) under oil at 37° C. in 6% $CO_2$ and humid atmosphere. Normal fertilization is confirmed by the presence of two pronuclei and two polar bodies 18 to 20 hours after microinjection or insemination. Early cleavage is observed at 25 or 27 hours after microinjection or insemination, respectively.

Three days after oocyte retrieval, embryo quality is graded from 1 to 4, according to the following morphological criteria: (a) number of blastomeres, (b) blastomere regularity and (c) fragmentation rate (Table I). An embryo was considered of top quality (grade 1 and 2) if 6 to 8 blastomeres of regular size with less than 25% fragmentation were observed (embryo with low fragmentation rate). Top quality embryos were transferred or frozen at day 3, whereas grade 3 and 4 embryos were discarded.

Four weeks after transfer, clinical pregnancy is confirmed by the presence of at least one gestational sac and the visualization of embryonic heart activity on ultrasound examination.

Accordingly, top quality embryo or competent embryo is an embryo of grade 1-2, with low fragmentation rate (equal or less than 25%), and having 6 to 8 blastomeres of regular size.

Accordingly, poor quality embryo or non competent embryo is an embryo of grade 3-4, with high fragmentation rate (more than 25%), and having fewer blastomeres (<6 cells at day 3) of regular or irregular size.

TABLE I

Embryo quality classification at day 3. Embryo quality was graded from 1 to 4 (1-2: top quality embryos; 3-4: poor quality embryos) based on the following morphological criteria (i) number of blastomeres, (ii) blastomere regularity and (iii) fragmentation rate.

| Day 3 | grade 1 | grade 2 | grade 3 | grade 4 | |
|---|---|---|---|---|---|
| number of blastomeres | 6-8 cells | 6-8 cells | 6-8 cells | <6 cells or >8 cells | — |
| blastomeres regularity | regular | regular | irregular | regular or irregular | regular or irregular |
| Fragmentation rate | 10% | 10-25% | 26-40% | <40% | >40% |

REFERENCES

Throughout this application, various references describe the state of the art to which this invention pertains. The disclosures of these references are hereby incorporated by reference into the present disclosure.

Cui X, Gao G, Yonezawa T, Dai G. Human Cartilage Tissue Fabrication Using Three-dimensional Inkjet Printing Technology. J Vis Exp. 2014.

Guerif F, Le Gouge A, Giraudeau B, Poindron J, Bidault R, Gasnier O, Royere D. Limited value of morphological assessment at days 1 and 2 to predict blastocyst development potential: a prospective study based on 4042 embryos. Hum Reprod. 2007 July; 22:1973-81.

Herrero J, Meseguer M. Selection of high potential embryos using time-lapse imaging: the era of morphokinetics. Fertil Steril. 2013 Mar. 15; 99:1030-4.

Hespel A M, Wilhite R, Hudson J. Invited review-applications for 3D printers in veterinary medicine. Vet Radiol Ultrasound. 2014.

Otolaryngol Head Neck Surg. 2014 March; 150(3):448-54. doi: 10.1177/0194599813518008. Epub 2013 Dec. 31.

Hochman J B, Kraut J, Kazmerik K, Unger B J. Generation of a 3D printed temporal bone model with internal fidelity and validation of the mechanical construct. Otolaryngol Head Neck Surg. 2014; 150:448-54.

Huisken J. Slicing embryos gently with laser light sheets. Bioessays. 2012; 34:406-11.

Huisken J, Stainier D Y. Selective plane illumination microscopy techniques in developmental biology. Development. 2009; 136:1963-75.

Huisken J, Swoger J, Del Bene F, Wittbrodt J, Stelzer E H. Optical sectioning deep inside live embryos by selective plane illumination microscopy. Science. 2004; 305:1007-9.

Kaufman M H, Brune R M, Baldock R A, Bard J B L, Davidson D. Computer-aided 3-D reconstruction of serially sectioned mouse embryos: its use in integrating anatomical organization. Int. J. Dev. Biol., 1997; 41:223-233.

Kaufmann A, Mickoleit M, Weber M, Huisken J. Multilayer mounting enables long-term imaging of zebrafish development in a light sheet microscope. Development. 2012; 139:3242-7.

Keller P J, Schmidt A D, Wittbrodt J, Stelzer E H. Reconstruction of zebrafish early embryonic development by scanned light sheet microscopy. Science. 2008; 322:1065-9.

Kim B J, Hong K S, Park K J, Park D H, Chung Y G, Kang S H. Customized cranioplasty implants using three-dimensional printers and polymethyl-methacrylate casting. J Korean Neurosurg Soc. 2012; 52:541-6.

Krzic U, Gunther S, Saunders T E, Streichan S J, Hufnagel L. Multiview light-sheet microscope for rapid in toto imaging. Nat Methods. 2012; 9:730-3.

Masselink W, Wong J C, Liu B, Fu J, Currie P D. Low-cost silicone imaging casts for zebrafish embryos and larvae. Zebrafish. 2014; 11:26-31.

Meseguer M, Herrero J, Tejera A, Hilligsøe K M, Ramsing N B, Remohí J. The use of morphokinetics as a predictor of embryo implantation. Hum Reprod. 2011; 26:2658-71.

Nakayama Y, Takewa Y, Sumikura H, Yamanami M, Matsui Y, Oie T, Kishimoto Y, Arakawa M, Ohmuma K, Tajikawa T, Kanda K, Tatsumi E. In-body tissue-engineered aortic valve (Biovalve type VII) architecture based on 3D printer molding. J Biomed Mater Res B Appl Biomater. 2014.

Nieman B J, Wong M D, Henkelman R M. Genes into geometry: imaging for mouse development in 3D. Curr Opin Genet Dev. 2011; 21:638-46.

Int J Comput Assist Radiol Surg. 2010 July; 5(4):335-41. doi: 10.1007/s11548-010-0476-x. Epub 2010 May 15.

Rengier F, Mehndiratta A, von Tengg-Kobligk H, Zechmann C M, Unterhinninghofen R, Kauczor H U, Giesel F L. 3D printing based on imaging data: review of medical applications. Int J Comput Assist Radiol Surg. 2010; 335-41.

Tan Y, Richards D J, Trusk T C, Visconti R P, Yost M J, Kindy M S, Drake C J, Argraves W S, Markwald R R, Mei Y. 3D printing facilitated scaffold-free tissue unit fabrication. Biofabrication. 2014; 6:024111.

Unger B J, Kraut J, Rhodes C, Hochman J. Design and Validation of 3D Printed Complex Bone Models with Internal Anatomic Fidelity for Surgical Training and Rehearsal. Stud Health Technol Inform. 2014.

Visser J, Melchels F P, Dhert W J, Malda J. Tissue printing; the potential application of 3D printing in medicine. Ned Tijdschr Geneeskd. 2013; 157:A7043.

Weber M, Huisken J. Light sheet microscopy for real-time developmental biology. Curr Opin Genet Dev. 2011; 21:566-72.

Wong M D, Maezawa Y, Lerch J P, Henkelman R M. Automated pipeline for anatomical phenotyping of mouse embryos using micro-CT. Development. 2014; 141:2533-41.

Wong M D, Dorr A E, Walls J R, Lerch J P, Henkelman R M. A novel 3D mouse embryo atlasbased on micro-CT. Development. 2012; 139:3248-56.

The invention claimed is:

1. An in vitro non-invasive method for determining the quality of at least one embryo comprising the steps of:
   isolating oocytes,
   performing in vitro fertilization of said oocytes,
   culturing said oocytes and identifying formation of the at least one embryo,
   providing serial image sections of the at least one embryo, said serial image sections being obtained by Optical Coherence Tomography (OCT), Magnetic Resonance Micro Imaging (µMPvI) or by standard optical microscopy or light sheet microscopy,
   based on the serial image sections, performing three dimensional reconstruction of the entire at least one embryo, including inner structures of the embryo,
   assessing one or more criteria selected from embryo morphology, fragmentation repartition, blastomere cleavage axis and cell repartition based on said three dimensional reconstruction, and,
   determining the quality of the at least one embryo based on the assessment of the one or more criteria.

2. The method according to claim 1,
   wherein said assessing step further comprises comparing the one or more criteria with the same one or more criteria from a three dimensional reconstruction of a control competent embryo and from a control non-competent embryo; and
   wherein the determining step further comprises concluding that the at least one embryo is competent when the one or more criteria are identical to the same one or more criteria in the control competent embryo, and concluding that the at least one embryo is non-competent when the one or more criteria are identical to the same one or more criteria in the control non-competent embryo.

3. The method according to claim 1 wherein
   embryo morphology is determined in view of the number of blastomeres, blastomere regularity and fragmentation rate, and
   the at least one embryo is identified as being competent when it has 6 to 8 blastomeres, blastomeres of regular size and a low fragmentation rate, and the embryo is identified as non-competent when the at least one embryo has less than 6 to 8 blastomeres, blastomeres of irregular size and a high fragmentation rate.

4. The method of claim 3, wherein the low fragmentation rate is equal to or less than 25%.

5. The method of claim 3, wherein the high fragmentation rate is greater than 25%.

6. A method for enhancing the pregnancy outcome of a patient comprising the steps of
   i) providing a plurality of embryos,
   ii) determining the quality of each embryo of said plurality of embryos by performing the method according to claim 1,
   iii) selecting the most competent embryo, and
   iv) implanting the most competent embryo selected at step iii) in the uterus of said patient.

7. The method of claim 1, wherein each of the at least one embryo is a human embryo.

8. The method of claim 1, wherein said serial image sections are obtained by Selective Plane Illumination Microscopy (SPIM).

* * * * *